United States Patent [19]

Sugimoto

[11] 4,101,646

[45] Jul. 18, 1978

[54] FERRITE VASCULAR CONTRAST MEDIA

[75] Inventor: Mitsuo Sugimoto, Tokyo, Japan

[73] Assignee: Rikagaku Kenkyusho, Japan

[21] Appl. No.: 252,519

[22] Filed: May 10, 1972

Related U.S. Application Data

[63] Continuation-in-part of Ser. No. 46,913, Jun. 17, 1970, abandoned.

[30] Foreign Application Priority Data

May 13, 1970 [JP] Japan .................................. 45-40656

[51] Int. Cl.$^2$ ............................................. A61K 29/02
[52] U.S. Cl. ........................................................ 424/4
[58] Field of Search ............................................. 424/4

[56] References Cited

U.S. PATENT DOCUMENTS

3,592,185  7/1971  Frei et al. ............................. 424/4 X

OTHER PUBLICATIONS

Whistler, Industrial Gums, Academic Press Inc., New York, (1959), p. 63.

*Primary Examiner*—Albert T. Meyers
*Assistant Examiner*—D. W. Robinson
*Attorney, Agent, or Firm*—Jacobs & Jacobs

[57] ABSTRACT

Vascular X-ray contrast media comprise ferrite powder coated with a negatively charged colloid such as silicate colloid, gold colloid, silver colloid or platinum colloid. Such media can be used for the medical X-ray diagnosis of small blood vessels. By applying an external magnetic field, the media can be maintained in the vessel or organ being examined.

4 Claims, 5 Drawing Figures

FERRITE VASCULAR CONTRAST MEDIA

CROSS-REFERENCE

This is a continuation-in-part of Ser. No. 46,913 filed June 17, 1970, now abandoned.

DETAILED DESCRIPTION

This invention relates to ferrite vascular contrast media having excellent magnetic properties and X-ray absorption, which are useful for the medical X-ray diagnosis of small vessels.

The constrast media for small vessels currently in use for the medical X-ray diagnosis of the organs are mostly aqueous iodine preparations. These media possess a number of disadvantages in actual use. Thus they are (1) apt to cause iodic allergy; (2) so stimulating to the heart that they sometimes induce cardial disorders; (3) depressive to the functions of the organs such as the kidney and liver; (4) deficient of the high contrasting power of barium sulfate; (5) difficult to keep in the same regions for extended periods of time, thus calling for great technical skill to set the suitable timing for taking the X-ray photograph; and (6) relatively expensive.

This invention provides new, excellent vascular contrast media which are free of the foregoing disadvantages. More particularly, the invention provides contrast media consisting of ferrites in the form of fine particles coated with negatively charged colloids.

This invention will be better understood from the following detailed description taken in conjunction with the accompanying drawings showing embodiments thereof. In the drawings.

Figure 1:
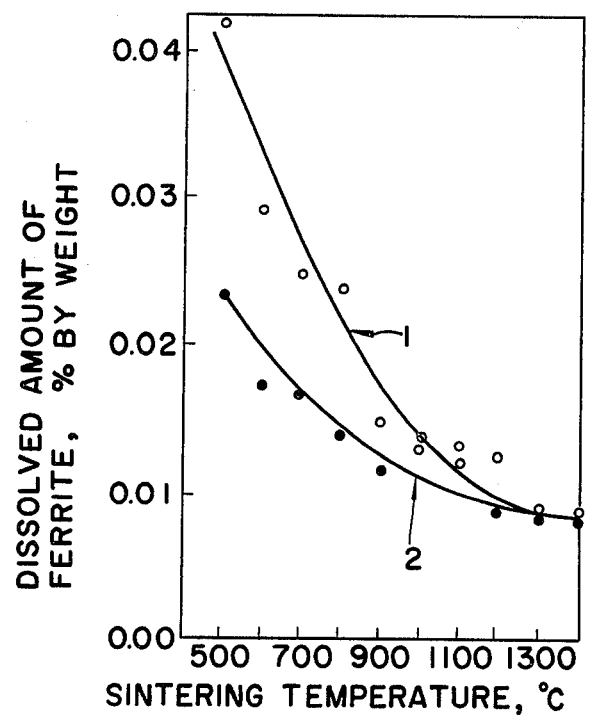
FIG. 1 is a graph illustrating the relationship between the firing temperature and the amounts of ferrites made of $Fe_2O_3$ in the form of either coarse particles or finely divided particles dissolved in an artificial gastric juice.

FIG. 1 illustrates the effect of particle size of the material $\alpha$-$Fe_2O_3$ upon the solubility of a Mn-Zn ferrite produced therefrom. The curve 1 represents the relationship between the firing temperature and the amount of dissolution in artificial gastric juice for Mn-Zn ferrite (with a composition of a molar ratio of 30 MnO: 20 ZnO: 50 $Fe_2O_3$) made of coarse-particle $\alpha$-$Fe_2O_3$(0.2 micron in diameter). The curve 2 presents a similar relationship for Mn-Zn ferrite made of an $\alpha$-$Fe_2O_3$ with high purity and fine particle size (0.05 micron in diameter) prepared by decomposing iron chloride in an oxygen atmosphere. Ferrites made of the fine-particle material, even if sintered at a low temperature, showed a small solubility. The sintering temperature, however, only has to be increased in order to reduce the amount of a ferrite that is dissolved in the artificial gastric juice. FIG. 1 indicates that the heating at a temperature of at least 1000° C is preferable and that when sintered at 1300° C are upwards, the solubility of ferrite is saturated. Higher sintering temperatures, on the other hand, render the ferrite so dense and tight that grounding of sintered ferrites into finely divided powder is rendered difficult. For these reasons, it is important for the manufacture of a ferrite contrast medium to fire the raw material mixture at a lowest possible temperature without fabricating it to any shape.

Since the material thus produced has low solubility in gastric juice, it is admirably suited as well for vascular contrast media, the acidity in human blood being very weak in comparison to that of gastric juice.

An injection of 0.1 to 0.2 ml portions of aqueous solutions of fine ferrite powders (0.05 to 1 micron in diameter) (in the form of solutions of ferrite powders in distilled water at the ratio by weight of 30 – 50 powder to 70 – 50 distilled water), intravascularly into the tails of rats or mice, produce very clear vasographs of the small vessels in the pancreas, kidney, liver, etc. Moreover, when a magnetic field of about 2,000 to 3,000 oersteds was applied externally by means of a permanent magnet or electromagnet, the ferrite powder can be moved to any desired spot, or kept in the same location, independently of the flow of the blood in the vessels. On the other hand, as the ferrite powder is moved through the blood vessels, the particles can gather and thereby induce clotting of the blood, or stick to the walls of the small vessels so as to interrupt the circulation of the blood.

The present invention provides vascular contrast media utilizing ferrites but eliminating the foregoing disadvantages. When a ferrite powder is mixed well with a negatively charged colloid, the ferrite composed essentially of $Fe_2O_3$, which is positively charged, is completely coated with the negatively charged colloid. The thus-coated individual ferrite particles can no longer gather easily because of the electrostatic repulsion. Since the walls of the small vessles are also negatively charged, the ferrite particles introduced into the small vessels are repulsed from the surrounding walls and therefore can not deposit on the walls. It has also been found that the excess of the colloid used for coating the particles of the ferrite powder keeps them randomly dispersed, thereby improving the properties of the contrast medium.

In the practice of this invention, the colloids which are employed to coat the ferrite particles are those which are negatively charged and of little or no toxicity to animals. These include such negatively charged colloids, for example, as those of gold, silver, platinum, silicate, starch, dyes and the like. The ferrite to be combined with any of these colloids can be composed of either one or more ferrites, including for example iron ferrite, manganese ferrite, nickel ferrite, copper ferrite, magnesium ferrite, cobalt ferrite, zinc ferrite, $\alpha$-ferric oxide, and ferro-magnetic ferric oxide. In any case, the ferrite is preferably one either sintered at a temperature of not lower than 1,000° C or synthesized under high oxygen atmosphere with pressure. Ferrites formed by alkali coprecipitation at room temperature are not suitable because those ferrites are incompletely crystallized and hence have insufficient X-ray absorbing power to give clear vasographs. The ferrite powders for the purpose of this invention are preferably of the particle sizes ranging from about 0.05 to 1 micron in diameter.

When a negatively charged colloid is to be added to a ferrite thereby to coat the ferrite particles, the mixing ratio should be, on the weight basis, about 80 to 50 parts of the colloid to about 20 to 50 parts of the ferrite. If the colloid proportion significantly exceeds the above range, the ferrite will have a seriously reduced X-ray absorbing power and if the proportion of colloid is too small the colloid will fail to coat the ferrite particles completely or make the ferrite preparation hard to inject. The ferrite particles properly coated with the negatively charged colloid can be readily dispersed in or diluted with a suitable liquid for injection purposes.

Figure 3:
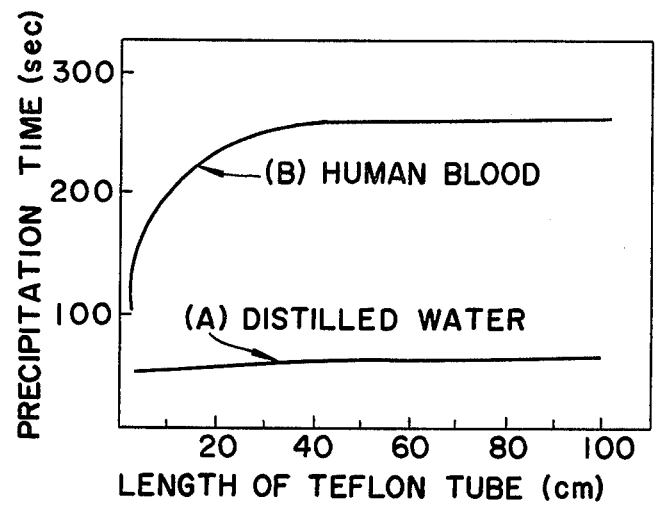
FIG. 3 is a graph illustrating the blood viscosity.

It might be expected that the coefficient of blood viscosity can be greatly effected by the ferric-containing contrast medium infused into small vessels. Measurements were taken of the viscosity characteristic of ferrite-containing contrast medium flowing in the small vessel and also of the time required for vertical precipitation of 15 cc distilled water in a Teflon fluorocarbon tube having an inside diameter of 1 mm. FIG. 3 illustrates the relationship between the precipitation time and the length of Teflon tube. The ratio of the precipitation time of human blood (B) to that of distilled water (A) indicates the viscosity coefficient of human blood. When the length of the tube exceeds 40 cm, both distilled water and human blood tend to have a saturation velocity of precipitation. In case of the length of the tube being below 40 cm, the precipitation time of distilled water increases rectilinearly as the length of the tube increases, while that of human blood tends to increase curvilinearly. This is probably due to the fact that erythrocytes can clump while the blood is flowing.

Figure 4:
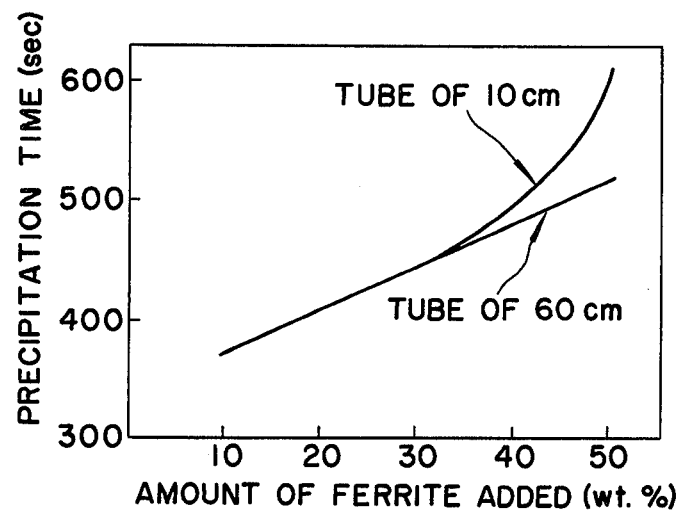
FIG. 4 is a graph representing the viscosity of human blood in which the ferrite media are suspended.

FIG. 4 shows the change of precipitation time of human blood in which ferrite is suspended. The precipitation time (apparent viscosity) increases curvilinearly in the tube having a length of 10 cm while it increases rectilinearly in the tube having a length of 60 cm. Since the viscosity of blood increases with the increase of the amount of ferrite added to blood, it is desirable that the amount of ferrite added is from about 20 to about 50 wt.%, preferably about 30 wt.%. Ferrite amounts substantially over 50 wt.% are thus undesirable while that of less than 20 wt.% will lower the function in X-ray photography.

Control of the injected ferrite media by movement of an externally applied magnetic field, is one advantageous aspect of this invention.

Figure 2:
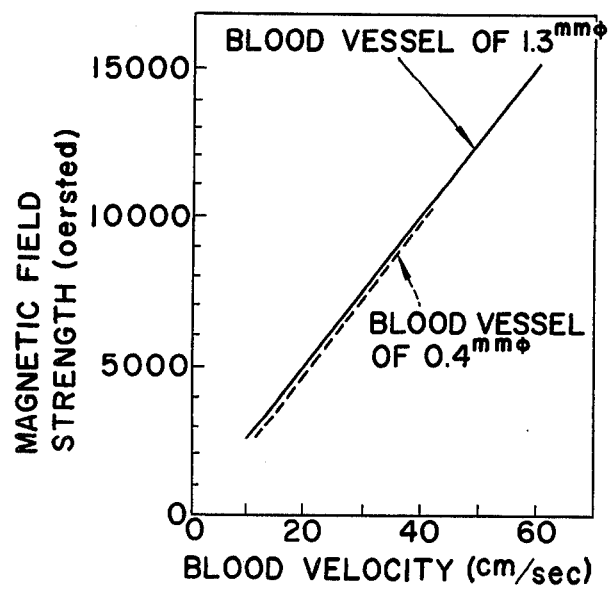
FIG. 2 is a graph of the relationship between the magnetic field strength and the blood velocity.

The strength of a magnetic field sufficient to keep the injected ferrite media in a given location in a vascular system will of course vary with the blood velocity. The relation between the blood velocity and the strength of a magnetic field is shown in FIG. 2, from which the strength of a magnetic field sufficient to stop the flow of the ferrite media, but not the blood, in the small vessels can be easily determined. For example, a magnetic field of about 2,000 oersteds should be applied externally to maintain the ferrite media in one position in blood flowing at a rate of 8 cm/sec. in a small vessel of 1.3 mm in diameter. Moreover, the ferrite media can be maintained in the applied location for long periods of time, and through the use of magnetic fields shall be easily removed from the small vessels after the observation by removal of the field. One particularly useful means of accomplishing this involves the use of a newly developed X-ray apparatus. This apparatus comprises a conventional X-ray apparatus, electromagnets and means to displace the electromagnets. More particularly, it comprises two electromagnets of 1500 and 2000 oersted respectively, and means to displace these electromagnets verticularly and in horizontal plane. When a magnetic field, for example, about 2,000 oersted is applied, the ferrite contrast media can be displaced or kept to any desired position.

Figure 5:
FIG. 5 is the X-ray photograph for the case of infusing the vascular contrast medium containing ferrite into the small vessel of a rat.

Using the above apparatus, an excellent image can be obtained with the ferrite contrast media of the present invention. FIG. 5 is the photograph demonstrative of a excellent image forming power when the ferrite vascular contrast media were injected into the small vessels of a rat.

The observed result demonstrates that the ferrite vascular contrast media in the blood vessels are displaceable to any desired location by the action of magnetic field and permit repeated and prolonged examination of the same location.

Intravenous injection to various animals of the ferrite vascular contrast media revealed no toxicity.

As described in the above tests, the vascular contrast media of the invention have great industrial and medical importance with advantages over the usual aqueous iodine preparation, i.e.: (1) by far the greater contrast-providing ability; (2) less adverse effect upon the functions of the organs; (3) no toxicity; (4) possibility of being kept in the same region for an extended period of time by means of a magnetic field applied; (5) no need of special skill in the radiography; and (6) availability at low cost.

Practical examples in the use of this invention are given below:

EXAMPLE 1

The ferrite was prepared by sintering the materials of $MnCO_3$, $Fe_2O_3$ and $ZnO$ at 1,300° C. for 5 hours. Thus, the manganese-zinc ferrite having the composition of $Mn_{0.6}$, $Zn_{0.4}$ and $Fe_2O_4$ was obtained.

The manganese-zinc ferrite obtained was milled into fine powder of $1\mu$ in diameter using a pulverizer of ball-mill for about 30 hours.

To remove impurities adhering to surface of the ferrite powder, the resultant was soaked in the solution of hydrochloric acid adjusted at pH 1.0 for about 1 hour, and thoroughly washed with water.

Next, to the solution dissolved in 100 cc of distilled water with 3.5 g of hydrochloric gold, 1 g of the manganese-zinc ferrite powder was added.

After heating at about 50° C, 3 g of potassium carbonate were added to the resultant with stirring and, 5 cc of formalin solution (0.3 cc of formalin solution being dissolved in 10 cc of the distilled water) were added to the resultant to form a vascular media coated with gold colloids of deep-red color.

After removal of excessive potassium carbonate and formalin from the media by washing with warm water, the test media were intravenously injected into the tail of a rat. As a result, extremely clear images of various internal organs were obtained (magnetic field applied being about 2,000 oersteds).

Also, when the solubility was examined by adding the ferrite powder coated with gold colloids into human blood, it was confirmed that the ferrite powder was not dissolved in human blood at all.

EXAMPLE 2

A suitable amount of potassium iodine was added to silver nitrate in order to form a negatively charged precipitate of silver iodide colloid. The resultant was thoroughly washed. At the ratio by weight, 70 parts of the colloid and 30 parts of manganese-zinc ferrite prepared by the same procedure as Example 1 were weighed and mixed up with stirring. A part of the test medium thus prepared was subjected to electrophoresis, when the ferrite particles were observed to move electrophoretically together with the colloid toward the positive electrode.

Also, when 0.2 ml of the test medium was intravascularly injected into the tail of a rat, extremely clear images of various internal organs compared with those of conventional vascular contrast media were obtained (magnetic field applied being about 2,000 oersteds).

EXAMPLE 3

0.5 g of the manganese-zinc ferrite prepared by the same procedure as Example 1 was added to 1.2 g of platinum chloride dissolved in 150 cc of distilled water, and 2 g of pure potassium carbonate were added to the resultant. After boiling the resultant was kept warm, and 3 cc of formalin solution were added to the resultant with stirring to form the ferrite powder coated with platinum colloids.

The resulting colloids were thoroughly washed with distilled water. 0.3 ml of the test media were intravenously injected to the tail of a rat.

After the lapse of about 10 minutes, X-ray diagnosis was done, and very clear contrast images of various internal organs compared with those of conventional vascular contrast media were obtained.

Next, a magnetic field of about 2,000 oersteds was applied to the paw of a dog, and the ferrite powder coated with gold colloids was intravenously injected into the paw of a dog.

As a result, it was confirmed by the X-ray diagnosis that the ferrite powder was kept in the applied location of a test animal.

Also, the ferrite powder injected into the view of a test animal was clearly showed by X-ray photograph.

EXAMPLE 4

The ferrite was prepared by sintering the materials of $NiCO_3$, $ZnO$ and $Fe_2O_3$ at 1,300° C. for 5 hours in air. Thus, the nickel-zinc ferrite having the composition of $Ni_{0.5}$, $Zn_{0.5}$ and $Fe_2O_4$ was obtained.

The nickel-zinc ferrite obtained was thoroughly milled into fine powder of 0.05$\mu$ in diameter using a pulverizer of ball-mill made of iron for about 40 hours.

To remove an iron contained in the ferrite powder, the resultant was soaked in the solution of hydrochloric acid adjusted at pH 0.5 for about 1 hour, and thoroughly washed with water.

A silicate colloid was formed of a dilute solution of sodium silicate and dilute hydrochloric acid, and the resulting colloid was thoroughly washed. On the basis of weight, 50 parts of the colloid and 50 parts of a nickel-zinc ferrite were weighed and mixed well with stirring. The ferrite particles thus obtained were found to be negatively charged.

A fraction of a milliliter of the test medium was intravascularly injected to the tail of a rat and a magnetic field of 2,000 oersteds was applied to the intestines by means of an electromagnet. X-ray observation clearly showed that in this way the ferrite contrast medium could be kept in the lower bowel for several hours. It was seen that, after the lapse of several hours, a part of the ferrite contrast medium began to move gradually upward to the lungs.

I claim:

1. A water dispersible composition for the preparation of a vascular radiographic contrast media, said composition comprising 20 to 50 parts by weight of at least one magnetic ferrite having a particle size of from about 0.05 to about 1 $\mu$ coated with from 80 to 50 parts by weight of a negatively charged colloid selected from the group consisting of colloidal gold, colloidal silver iodide, colloidal platinum and colloidal silicate.

2. A composition according to claim 1, wherein the magnetic ferrite is selected from the group consisting of copper-zinc ferrite, nickel-zinc ferrite, manganese-zinc ferrite, zinc ferrite, magnesium ferrite, $\alpha$-ferric oxide and ferrosoferric oxide.

3. A contrast media comprising a composition according to claim 1, dispersed in a pharmaceutically acceptable aqueous carrier.

4. A contrast media according to claim 3 wherein the ratio by weight of composition to carrier is 30 to 50 : 70 to 50.

* * * * *